United States Patent [19]

Deppe et al.

[11] Patent Number: 4,559,819
[45] Date of Patent: Dec. 24, 1985

[54] SELECTING THE CUT-OFF END PORTION OF ROLLED SHEET STOCK

[75] Inventors: Gerd-Joachim Deppe, Duisburg; Hans H. Ettwig, Rheinberg; Heinz Schneider, Düsseldorf; Wolfram Hof, Mülheim, all of Fed. Rep. of Germany

[73] Assignee: Mannesmann Aktiengesellschaft, Düsseldorf, Fed. Rep. of Germany

[21] Appl. No.: 495,153

[22] Filed: May 17, 1983

[51] Int. Cl.[4] .......................... B21B 37/10; G01J 5/02
[52] U.S. Cl. .......................................... 73/159; 72/13; 250/342; 374/137
[58] Field of Search ...................... 73/159; 374/6, 137, 374/4; 364/475; 72/13, 14

[56] References Cited

U.S. PATENT DOCUMENTS

| | | | |
|---|---|---|---|
| 3,483,721 | 12/1969 | Apple et al. | 72/13 |
| 3,782,192 | 1/1974 | Sandblom | 374/6 |
| 3,871,212 | 3/1975 | Neugroschl | 73/159 |
| 3,974,248 | 8/1976 | Atkinson | 73/159 |
| 4,104,723 | 8/1978 | Tokuno et al. | 364/475 |
| 4,157,039 | 6/1979 | Kilmister | 374/137 |
| 4,170,155 | 10/1979 | Saito et al. | 364/475 X |
| 4,274,273 | 6/1981 | Fapiano et al. | 72/13 |
| 4,324,138 | 3/1982 | Davis et al. | 374/137 X |
| 4,439,049 | 3/1984 | Hoogendoorn | 374/137 X |

FOREIGN PATENT DOCUMENTS 0116873 12/1978 Japan ...................................... 374/6

Primary Examiner—Daniel M. Yasich
Attorney, Agent, or Firm—Ralf H. Siegemund

[57] ABSTRACT

The method as described is an attempt to minimize the length of the sheet stock to be cut off at the end of rolled stock as waste. This minimizing should be carried out on-line, and it is suggested that immediately following straightening the rolled sheet stock, the surface temperature profile in the end region and beyond is measured in a contactless method for determining on-line the place of cutting; cutting may then be controlled accordingly.

3 Claims, 1 Drawing Figure

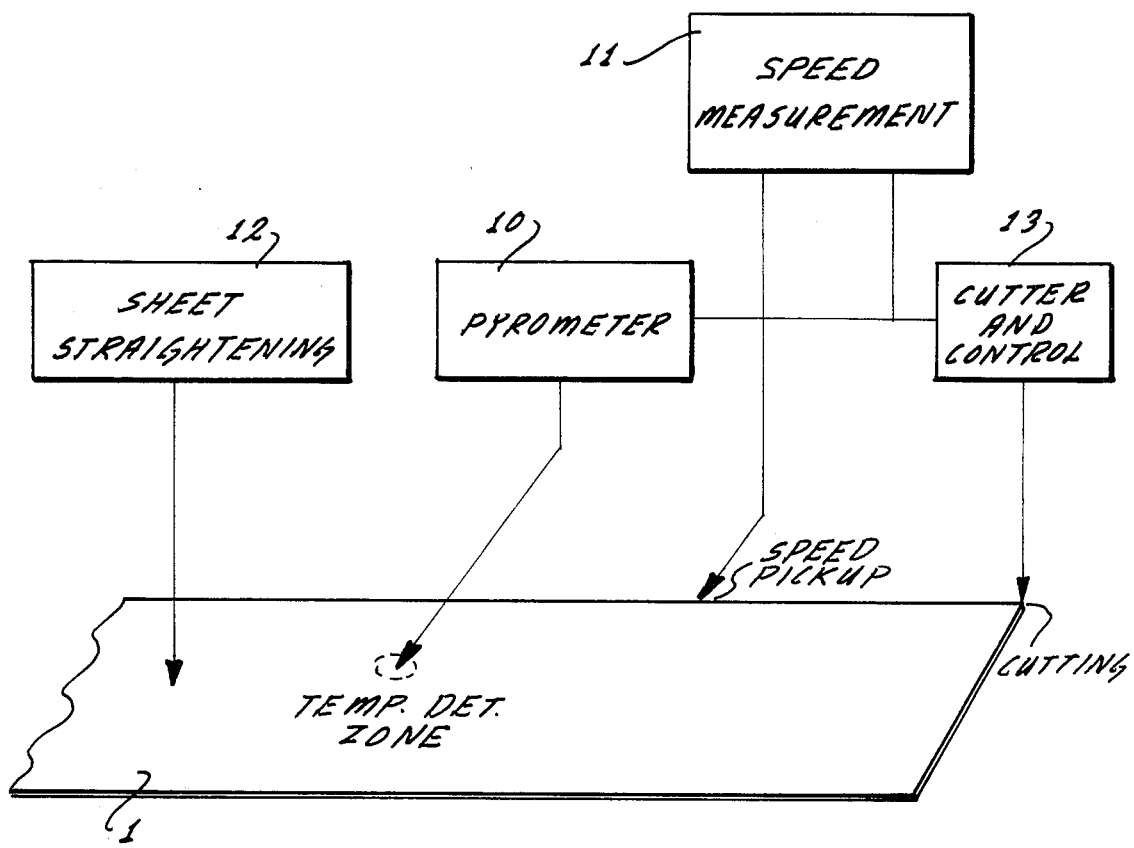

SELECTING THE CUT-OFF END PORTION OF ROLLED SHEET STOCK

BACKGROUND OF THE INVENTION

The present invention relates to a method for automatically selecting the end cut in thermo mechanically rolled metal sheet or plate stock under consideration of permissable elastic limit and yield point of the material.

Cutting the end of sheet stock following rolling thereof is usually carried out on the basis of empirically ascertained data. Samples taken from the cooled sheet stock are tested as to the suitability of the cut at a chosen location. These samples are taken under consideration of the requirement that the mechanical properties of the sheet should remain uniform or at least essentially uniform over the length of the respective sheets or plate.

Measuring in the stated manner does not permit optimizing the end cutting. Therefore, for reasons of safety, one cuts larger end length than is really necessary.

DESCRIPTION OF THE INVENTION

It is an object of the present invention to provide a new and improved method for automatically ascertaining the location of the end cut of thermo mechanically rolled sheet or plate stock whereby the length of the sheet end to be separated by cutting is to be minimized in an on-line operation.

It is a particular object of the present invention to provide a new and improved method for ascertaining the desirable location for the end cut on thermo mechanically rolled sheet or plate stock under consideration of the permissable yield point and the elastic limit of the material.

In accordance with the preferred embodiment of the preferred invention, it is suggested that immediately following the straightening of the rolled sheet stock, the length of the portion at the end to be cut be determined in dependence upon a contactless acquired surface temperature profile. The temperature is measured through an incremental area constituting a measuring spot having particular dimensions in geometry. A longitudinal coordinate is associated with the temperature profile in that the respective locations from which the data have been taken are ascertained by means of integrating the speed of advance of the sheet stock after rolling The resulting measurements can be used directly for controlling timing of the cutting.

The drawing illustrates schematically the practicing of the inventive method.

The invention is based on the consideration that the ends of each sheet 1 after the rolling are noticeably darker and therefore colder than the more central portion of the freshly rolled sheet or plate stock. Experiments and analytical investigations have demonstrated that there is relationship between the surface temperature profile and the yield limit such that the yield point and elastic limit increases towards the ends of the material. The invention suggests, as stated, that the surface temperature profile be taken near the ends and this reduces the waste resulting from severed end pieces. Moreover, the overall mechanical properties are equalized over the remaining sheet stock lengths.

The inventive method is preferably practiced by means of suitable measuring equipment, including a pyrometer 10 and a velometer 11 (i.e. speed measuring devices) and the corresponding data acquisition devices as shown in the drawing which are known per se and are readily applicable to the material and the rolling process as stated. It is important that the temperature measuring result is acquired by equipment 10 independently from any variations in the speed of the sheet stock. It should be observed that upon rolling the sheet stock, i.e., immediately thereafter, the rolled sheets are straightened (12). The temperature measurement is now carried out in the straightening machine. For example, a suitably placed pyrometer such as 10 responds to a particular measuring area on the passing sheet and as the sheet moves, the temperature profile of the passing sheet stock instruments are ascertained. The measuring spot or immediate limited observation field may have oval or rectangular configuration.

It can readily be seen that the output of the pyrometer 10 represents the ascertained temperature of the moving sheet stock and by means of the velometer 11, these temperature readings are associated with a longitudinal coordinate of the sheet and passed to a computer. The program of the computer provides a corrective computation and associates the temperature profile over the length of the sheet stock with coordinates thereof arrived at by integrated speed measurement. The determination of the length of the sheet stock portion to be cut up is carried out in operation, i.e. on-line and by means of a computer which will furnish the appropriate control signals to a cutter 13 thereby minimizing the cutting of waste.

The invention is not limited to the embodiments described above; but all changes and modifications thereof, not constituting departures from the spirit and scope of the invention, are intended to be included.

We claim:

1. Method of automatically selecting the length of an end portion to be cut off, of a thermo mechanically rolled sheet or plate stock under consideration of admissable yield point values, there being a straightening step provided to follow the rolling of sheet stock, comprising the step of contactless measuring, the velocity and the surface temperature of the sheet stock without physical engagement and immediately following the straightening and obtaining a temperature profile from the velocity and temperature measurements;

determining and selecting the length of the end to be cut off the sheet, on-line and in dependence upon the progressively acquired surface temperature profile; and cutting off an end portion as so determined and selected.

2. Method as in claim 1 and including selecting an incremental area from which to measure the temperature and; further including causing portions of the sheet stock to pass said area.

3. Method as in claim 1 and including the step of associating measurement values of the temperature with locations on the sheet stock by means of integrating velocity measurements of the sheet stock as it passes through.

* * * * *